US011701237B2

(12) United States Patent
Stinchfield et al.

(10) Patent No.: US 11,701,237 B2
(45) Date of Patent: *Jul. 18, 2023

(54) SPINAL IMPLANT SYSTEM

(71) Applicant: Warsaw Orthopedic, Inc., Warsaw, IN (US)

(72) Inventors: Thomas J. Stinchfield, Germantown, TN (US); Julien J. Prevost, Memphis, TN (US); Robert M. Loke, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 41 days.

This patent is subject to a terminal disclaimer.

(21) Appl. No.: 17/200,496

(22) Filed: Mar. 12, 2021

(65) Prior Publication Data

US 2021/0196476 A1    Jul. 1, 2021

Related U.S. Application Data

(63) Continuation of application No. 15/896,936, filed on Feb. 14, 2018, now Pat. No. 10,987,229.

(51) Int. Cl.
*A61F 2/44*     (2006.01)
*A61F 2/30*     (2006.01)
(Continued)

(52) U.S. Cl.
CPC .............. *A61F 2/4465* (2013.01); *A61F 2/44* (2013.01); *A61F 2/446* (2013.01); *A61F 2/4425* (2013.01);
(Continued)

(58) Field of Classification Search
CPC .......... A61F 2/446; A61F 2/4425; A61F 2/44; A61F 2/442; A61F 2/4455; A61F 2/4465;
(Continued)

(56) References Cited

U.S. PATENT DOCUMENTS 6,808,538 B2    10/2004  Paponneau
7,544,208 B1     6/2009  Mueller et al.
(Continued)

FOREIGN PATENT DOCUMENTS

CN    104936555    9/2015
CN    106999288    8/2017
(Continued)

OTHER PUBLICATIONS

International Search Report and Written Opinion dated May 29, 2019 for PCT/US2019/017576.
(Continued)

*Primary Examiner* — Marcela I. Shirsat

(57) ABSTRACT

A spinal implant system is provided for bridging an intervertebral space between vertebral bodies bordering the intervertebral space. The spinal implant system includes at least one adjustable end cap and a spinal implant. The end cap can be used with additional end caps and/or the spinal implant. Multiple end caps can be stacked on top of one another, and one end cap can be attached to a first end of the spinal implant, and another end cap can be attached to a second end of the spinal implant. Thus, one or more of the end caps can be attached to either end of the spinal implant.

20 Claims, 13 Drawing Sheets

(51) Int. Cl.
*A61B 17/02* (2006.01)
*A61B 17/70* (2006.01)

(52) U.S. Cl.
CPC ... *A61B 17/7059* (2013.01); *A61B 2017/0256* (2013.01); *A61F 2/442* (2013.01); *A61F 2/4455* (2013.01); *A61F 2002/3055* (2013.01); *A61F 2002/30224* (2013.01); *A61F 2002/30495* (2013.01); *A61F 2002/30507* (2013.01); *A61F 2002/30523* (2013.01); *A61F 2002/30538* (2013.01); *A61F 2002/443* (2013.01); *A61F 2002/448* (2013.01); *A61F 2002/4415* (2013.01)

(58) Field of Classification Search
CPC .......... A61F 2/4611; A61F 2002/30224; A61F 2002/443; A61F 2002/3055; A61F 2002/30601; A61F 2002/30841; A61F 2002/30507; A61F 2002/2835; A61F 2002/30235; A61F 2002/30785; A61F 2002/305; A61F 2002/30538; A61F 2002/30495; A61F 2002/30523; A61B 17/7059; A61B 2017/0256
USPC ............................................ 623/17.11–17.16
See application file for complete search history.

(56) References Cited

U.S. PATENT DOCUMENTS

| | | | |
|---|---|---|---|
| 8,202,321 B2 | 6/2012 | Gener | |
| 8,211,178 B2 | 7/2012 | Melkent et al. | |
| 8,372,151 B2 | 2/2013 | Hsu et al. | |
| 8,613,768 B2 | 12/2013 | Biedermann et al. | |
| 8,945,228 B2 | 2/2015 | Popa et al. | |
| 9,333,088 B2 | 5/2016 | Berger et al. | |
| 9,393,128 B2 | 7/2016 | Hansell et al. | |
| 9,801,730 B2 | 10/2017 | Howard et al. | |
| 9,974,663 B2 | 5/2018 | Stinchfield et al. | |
| 10,226,352 B2 | 3/2019 | Lorenz et al. | |
| 10,987,229 B2 * | 4/2021 | Stinchfield | A61F 2/4465 |
| 2009/0138089 A1 | 5/2009 | Doubler et al. | |
| 2010/0324686 A1 | 12/2010 | Gerner | |
| 2014/0135933 A1 | 5/2014 | Mcclintock et al. | |
| 2014/0207236 A1 | 7/2014 | Prevost et al. | |
| 2016/0100955 A1 | 4/2016 | Stinchfield et al. | |
| 2016/0175103 A1 | 6/2016 | Howard | |
| 2016/0175108 A1 | 6/2016 | Howard et al. | |
| 2016/0193057 A1 | 7/2016 | Rhoda | |
| 2017/0007423 A1 | 1/2017 | McLaughlin et al. | |
| 2017/0360572 A1 | 12/2017 | Bannigan et al. | |

FOREIGN PATENT DOCUMENTS

| | | |
|---|---|---|
| WO | 2008065450 | 6/2008 |
| WO | 2017049268 | 3/2017 |

OTHER PUBLICATIONS

Ecd—Expandable Corpectomy Device Surgical Technique Depuy Synthes, Dec. 2015.
Extended European Search Report dated Oct. 10, 2021 for EP Application No. 19754596.5.
Chinese Search Report and First Office Action dated Feb. 20, 2023 in China Application No. 201980010036.9 with Translation.

* cited by examiner

SPINAL IMPLANT SYSTEM

CROSS-REFERENCE TO RELATED APPLICATIONS

The present application is a continuation of U.S. application Ser. No. 15/896,936, filed Feb. 14, 2018; all of which is hereby incorporated by reference in its entirety.

BACKGROUND OF THE INVENTION

The present invention relates to a spinal implant system employing an end cap for use with additional end caps and/or a spinal implant or spinal implants. More particularly, the present invention relates to a modular spinal implant system using an end cap that can be attached to additional end caps and/or a spinal implant to increase the height of the modular spinal implant system so that the system is sized appropriately for an intervertebral space. More specifically, the present invention relates to a modular spinal implant system that allows one or more adjustable end caps to be stacked on either end of a spinal implant or spinal implants to increase the height of the spinal implant system, and allows the adjustable end caps to be adjusted to create angularity between an upper surface and a lower surface of the spinal implant system.

Spinal disorders oftentimes requires removal of one or more vertebral bodies from the spine of a patient. An intervertebral space between the remaining vertebral bodies is typically bridged by instrumentation to stabilize the spine. Various spinal implants such as, for example, corpectomy devices, whether unexpandable or expandable, typically have been used as the instrumentation to stabilize the spine. Such corpectomy devices can have end portions that afford angular adjustment so that the angularity between an upper surface and a lower surface of the corpectomy device can be adjusted.

However, there is a need for additional adjustability of the height and/or the angularity of the ultimate construct for implantation in the intervertebral space. The present invention is directed to one or more end caps that can be attached to either an unexpandable or an expandable spinal implant to provide for a spinal implant system. One or more of the end caps can be attached to either of the ends of the spinal implant to increase the height of the spinal implant system, and the one or more end caps each can have angular adjustment features that allow the angularity between an upper surface and a lower surface of the spinal implant system to be adjusted. As such, the configuration of the spinal implant system provided by the one or more end caps can be adjusted to fit the intervertebral space.

SUMMARY OF THE INVENTION

The present invention in one preferred embodiment contemplates a spinal implant system including a spinal implant having a first end, an opposite second end, a height between the first end and the second end, the spinal implant including a first flange portion provided at the first end, a second flange portion provided at the second end, a first recess provided adjacent the first flange portion, and a second recess provided adjacent the second flange portion, the first flange portion and the second flange portion each including a perimeter surface extending at least partially along the first flange portion and the second flange portion; and an end cap having a first end and an opposite second end, the end cap having a base portion including a lower portion and an upper portion, the lower portion being provided at the first end of the end cap, and the upper portion extending from the lower portion to adjacent the second end of the end cap, the lower portion including a perimeter, a lower surface, and a plurality of sidewall portions, the plurality of sidewall portions being spaced apart from one another adjacent the perimeter of the lower portion, at least two of the plurality of sidewall portions being spaced apart from one another across a portion of the lower surface, the lower surface and inner surfaces of the plurality of sidewall portions defining a first cavity, and the inner surfaces of at least two of the plurality of sidewall portions each including a tab extending into the first cavity, and the upper portion including a first end, an opposite second end, a first mid-longitudinal axis extending through the first end and the second end, and an exterior surface portion extending between the first end and the second end, the first end of the upper portion being attached to the lower portion, and the exterior surface portion including a tapered portion adjacent the second end of the upper portion, the end cap having a body portion including a sidewall portion, a third flange portion, and a third recess, the sidewall portion extending from adjacent the first end of the end cap to adjacent the second end of the end cap, the third flange portion being provided at the second end of the end cap, and the third recess provided in the sidewall portion adjacent the third flange, the sidewall portion having a second mid-longitudinal axis and defining an interior cavity for receiving a portion of the upper portion of the base portion, the interior cavity having an engagement surface therein for contacting at least a portion of the tapered portion of the upper portion of the base portion; where the body portion is positionable with respect to the base portion by adjusting the position of the engagement surface of the interior cavity of the body portion on the tapered portion of the upper portion of the base portion; and where the first cavity of the end cap is configured to receive one of the first flange portion of the spinal implant and the second flange portion of the spinal implant, the tabs of the end cap being received in one of the first recess and the second recess corresponding to the one of the first flange and the second flange to facilitate attachment of the end cap to the spinal implant.

The present invention in another preferred embodiment contemplates a spinal implant system including a spinal implant having a first end, an opposite second end, and a height between the first end and the second end, the spinal implant including a first flange portion provided at the first end, a second flange portion provided at the second end, a first recess provided adjacent the first flange portion, and a second recess provided adjacent the second flange portion, the first flange portion and the second flange portion each including a perimeter surface extending at least partially along the first flange portion and the second flange portion; a first end cap having a first end and an opposite second end, the first end cap having a first base portion including a lower portion and an upper portion, the lower portion of the first base portion being provided at the first end of the first end cap, and the upper portion of the first base portion extending from the lower portion of the first base portion to adjacent the second end of the first end cap, the lower portion of the first base portion including a perimeter, a lower surface, and a plurality of sidewall portions, the plurality of sidewall portions of the lower portion of the first base portion being spaced apart from one another adjacent the perimeter of the lower portion of the first base portion, at least two of the plurality of sidewall portions of the lower portion of the first base portion being spaced apart from one another across a portion of the lower surface, the lower surface of the lower portion of the first base portion and inner surfaces of the plurality of sidewall portions of the lower portion of the first base portion defining a first cavity, and the inner surfaces of at least two of the plurality of sidewall portions of the lower portion of the first base portion each including a tab extending into the first cavity, and the upper portion of the first base portion including a first end, an opposite second end, and an exterior surface portion extending between the first end and the second end of the upper portion of the first base portion, the first end of the upper portion of the first base portion being attached to the lower portion of the first base portion, and the exterior surface portion of the upper portion of the first base portion including a tapered portion adjacent the second end of the upper portion of the first base portion, the first end cap having a first body portion including a sidewall portion, a third flange portion, and a third recess, the sidewall portion of the first body portion extending from adjacent the first end of the first end cap to adjacent the second end of the first end cap, the third flange portion of the first body portion being provided at the second end of the first end cap, and the third recess of the first body portion provided in the sidewall portion of the first body portion adjacent the third flange portion of the first body portion, the sidewall portion of the first body portion defining an interior cavity for receiving a portion of the upper portion of the first base portion, the interior cavity of the first body portion having an engagement surface therein for contacting at least a portion of the tapered portion of the upper portion of the first base portion; and a second end cap having a first end and an opposite second end, the second end cap having a second base portion including a lower portion and an upper portion, the lower portion of the second base portion being provided at the first end of the second end cap, and the upper portion of the second base portion extending from the lower portion of the second base portion to adjacent the second end of the second end cap, the lower portion of the second base portion including a perimeter, a lower surface, and a plurality of sidewall portions, the plurality of sidewall portions of the lower portion of the second base portion being spaced apart from one another adjacent the perimeter of the lower portion of the second base portion, at least two of the plurality of sidewall portions of the lower portion of the second base portion being spaced apart from one another across a portion of the lower surface of the lower portion of the second base portion, the lower surface and inner surfaces of the plurality of sidewall portions of the lower portion of the second base portion defining a second cavity, and the inner surfaces of at least two of the plurality of sidewall portions of the lower portion of the second base portion each including a tab extending into the second cavity, and the upper portion of the second base portion including a first end, an opposite second end, and an exterior surface portion extending between the first end and the second end of the upper portion of the second base portion, the first end of the upper portion of the second base portion being attached to the lower portion of the second base portion, and the exterior surface portion of the upper portion of the second base portion including a tapered portion adjacent the second end of the upper portion of the second base portion, the second end cap having a second body portion including a sidewall portion, a fourth flange portion, and a fourth recess, the sidewall portion of the second body portion extending from adjacent the first end of the second end cap to adjacent the second end of the second end cap, the fourth flange portion of the second body portion being provided at the second end of the second end cap, and the fourth recess of the second body portion provided in the sidewall portion of the second body portion adjacent the fourth flange portion of the second body portion, the sidewall portion of the second body portion defining an interior cavity for receiving a portion of the upper portion of the second base portion, the interior cavity of the second body portion having an engagement surface therein for contacting at least a portion of the tapered portion of the upper portion of the second base portion; where the first cavity of the first end cap is configured to receive one of the first flange portion of the spinal implant and the second flange portion of the spinal implant, and the second cavity of the second end cap is configured to receive the third flange portion of the first end cap, or the other of the first flange portion and the second flange portion, the tabs of the first end cap being received in one of the first recess and the second recess corresponding to the one of the first flange portion and the second flange portion to facilitate attachment of the first end cap to the spinal implant, and the tabs of the second end cap being received in the third recess or the other of the first recess and the second recess corresponding to the third flange portion or the other of the first flange portion and the second flange portion to facilitate attachment of the second end cap to the first end cap or the spinal implant.

The present invention in yet another preferred embodiment contemplates a method of sizing for and inserting in an intervertebral space componentry of a spinal implant system, the method including determining a distance and an angularity between vertebral bodies bordering an intervertebral space; selecting an expandable spinal implant and at least one end cap sized to fill the distance between the intervertebral space; the spinal implant having a first end, an opposite second end, and a height between the first end and the second end, the spinal implant including a first flange portion provided at the first end, a second flange portion provided at the second end, a first recess provided adjacent the first flange portion, and a second recess provided adjacent the second flange portion, the first flange portion and the second flange portion each including a perimeter surface extending at least partially along the first flange portion and the second flange portion, and a end cap having a first end and an opposite second end, the end cap having a base portion including a lower portion and an upper portion, the lower portion being provided at the first end of the end cap, and the upper portion extending from the lower portion to adjacent the second end of the end cap, the lower portion including a perimeter, a lower surface, and a plurality of sidewall portions, the plurality of sidewall portions being spaced apart from one another adjacent the perimeter of the lower portion, at least two of the plurality of sidewall portions being spaced apart from one another across a portion of the lower surface, the lower surface and inner surfaces of the plurality of sidewall portions defining a first cavity, and the inner surfaces of at least two of the plurality of sidewall portions each including a tab extending into the first cavity, and the upper portion including a first end, an opposite second end, a first mid-longitudinal axis extending through the first end and the second end, and an exterior surface portion extending between the first end and the second end, the first end of the upper portion being attached to the lower portion, and the exterior surface portion including a tapered portion adjacent the second end of the upper portion, the end cap having a body portion including a sidewall portion and a third flange portion, the sidewall portion extending from adjacent the first end of the end cap to adjacent the second end of the end cap, and the third flange portion being provided at the second end of the end cap, the sidewall portion having an interior cavity for receiving a portion of the upper portion of the base portion, the interior cavity having an engagement surface therein for contacting at least a portion of the tapered portion of the upper portion of the base portion, attaching the end cap to one of the first flange portion and the second flange portion by receiving the one of the first flange portion and the second flange portion in the first cavity and inserting the tabs of the at least two of the plurality of sidewall portions into one of the first recess and the second recess corresponding to the one of the first flange and the second flange; and inserting the expandable spinal implant and the end cap attached thereto into the intervertebral space by contacting the third flange portion of the end cap with one of the vertebral bodies bordering the intervertebral space, and contacting the other of the first flange portion and the second flange portion with the other of the vertebral bodies bordering the intervertebral space.

DETAILED DESCRIPTION OF THE PREFERRED EMBODIMENT

A spinal implant system according to an embodiment of the present invention is disclosed in FIGS. 1-11. The spinal implant system is employed, for example, with a surgical procedure, including percutaneous, mini-open, and open surgical techniques to deliver and introduce instrumentation and/or an implant to a surgical site in the body of a patient. The instrumentation and/or the implant can include, for example, a spinal implant system including a spinal implant or spinal implants such as, for example, a corpectomy device, and the spinal implant system can be implanted into a section of the spine of the patient. The spinal implant system may be employed with surgical procedures such as fusion, non-fusion, and/or fixation treatments that employ implants to restore the mechanical support function of the vertebrae of the patient. These procedures can include, for example, corpectomy and discectomy procedures Thus, the intervertebral space formed by removal of one or more vertebral bodies and one or more discs, and the spinal implant system is used to bridge the intervertebral space between vertebral bodies bordering the intervertebral space.

Figure 4:
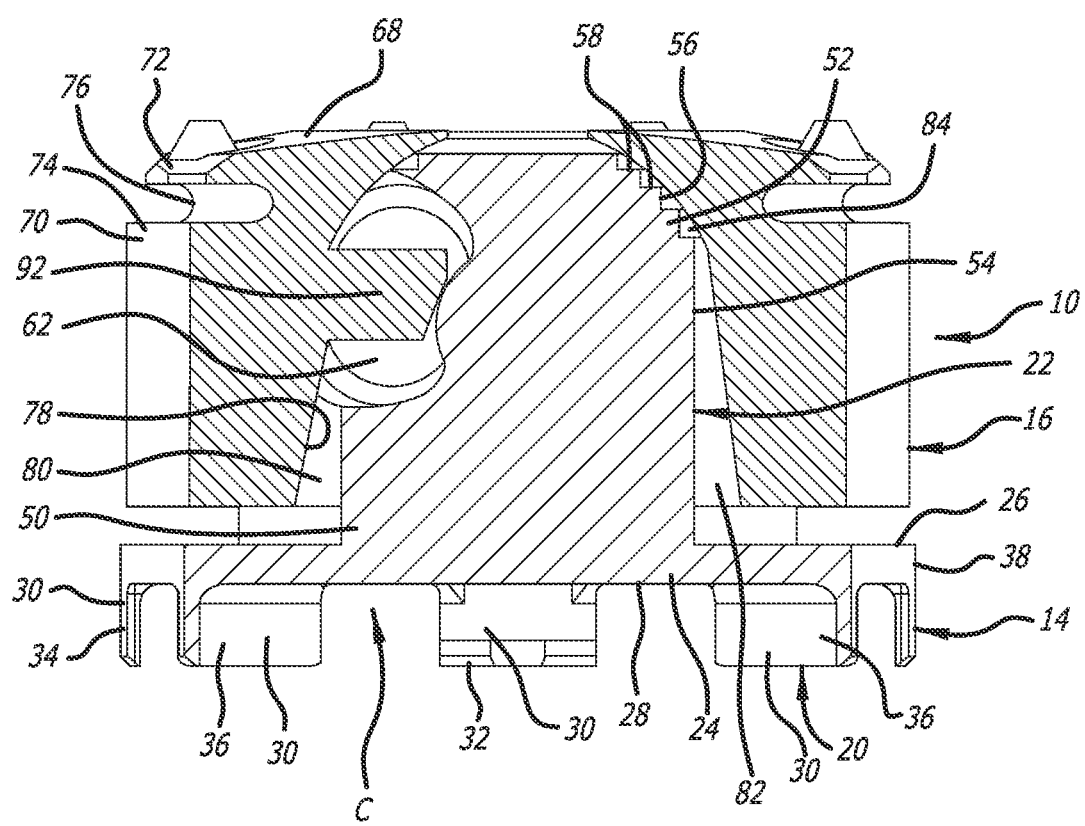
FIG. 4 is a cross-sectional view of the end cap of FIG. 1 taken along Line 4-4 of FIG. 3.
Figure 5:
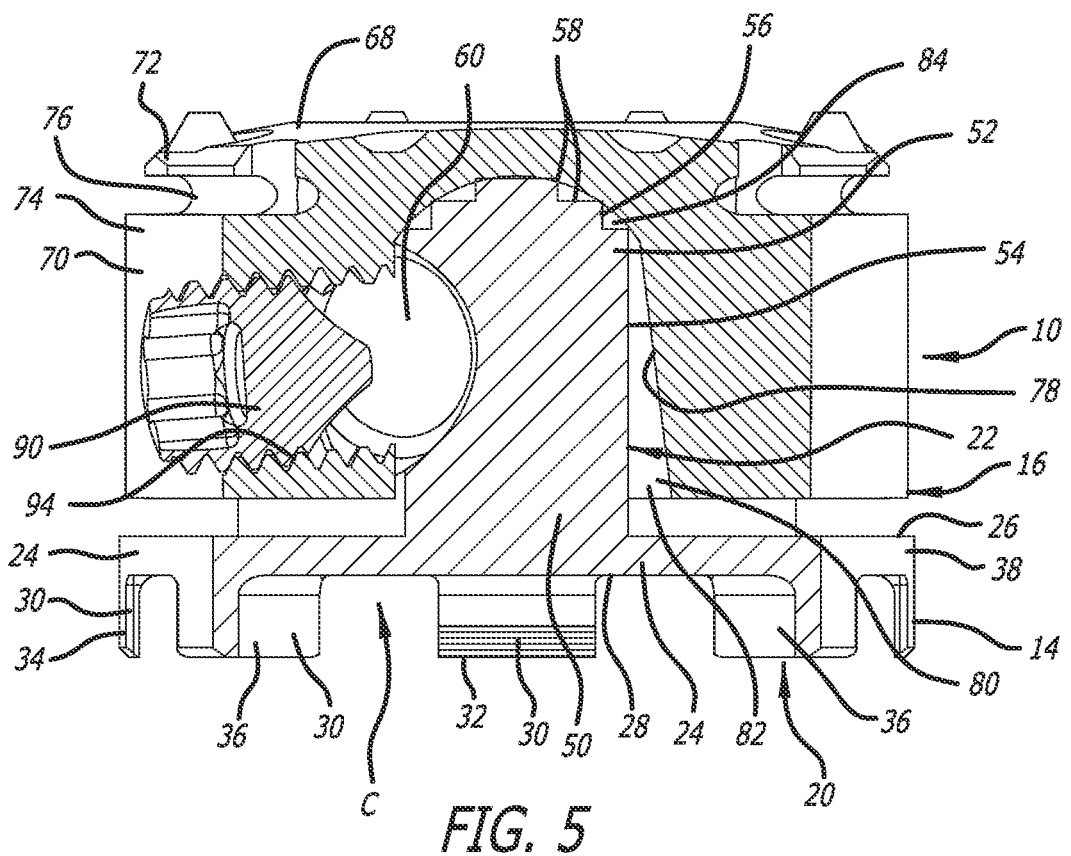
FIG. 5 is a cross-sectional view of the end cap of FIG. 1 taken along Line 5-5 of FIG. 3.
Figure 6:
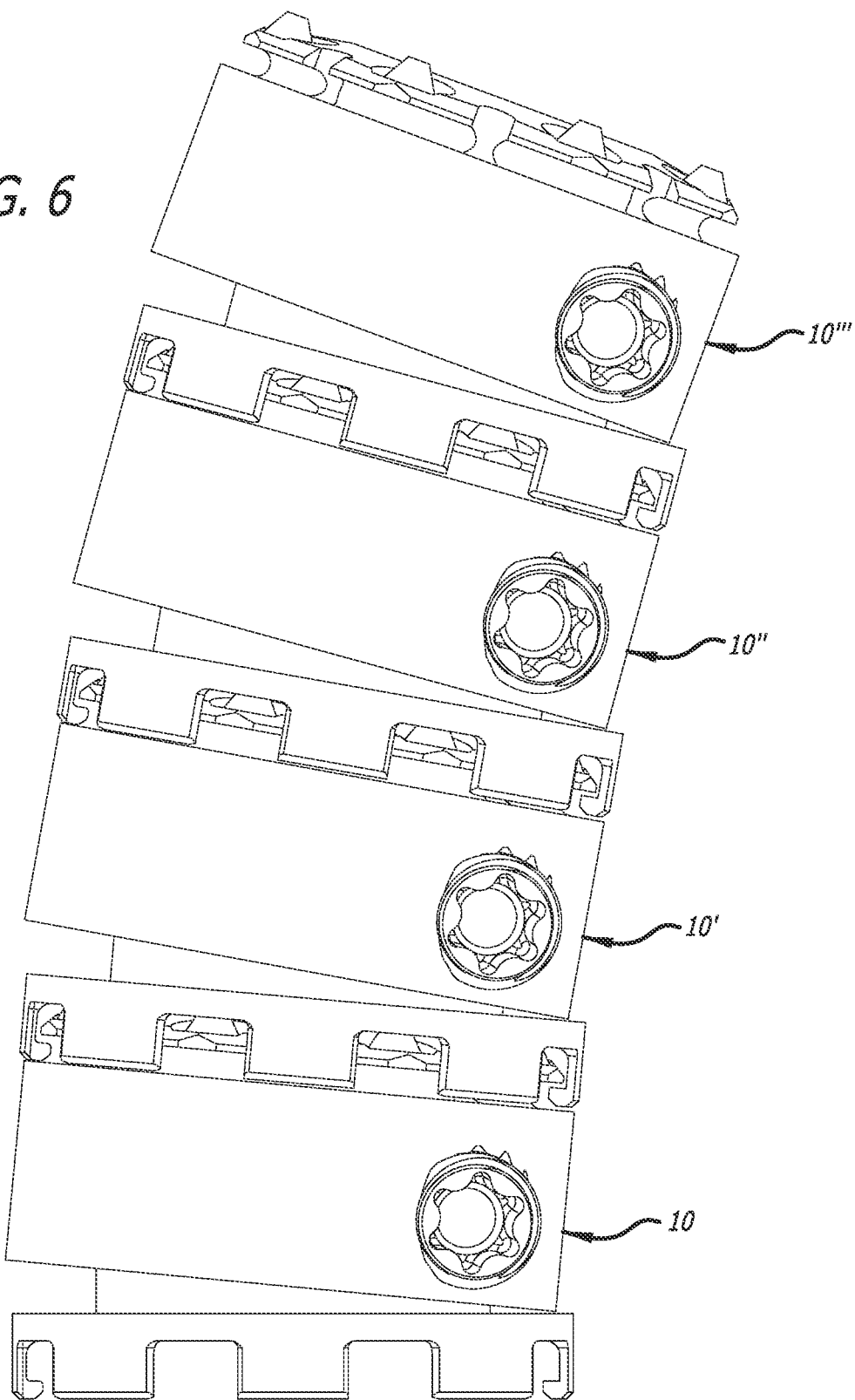
FIG. 6 is a front elevational view of various end caps of FIG. 1 stacked on top of one another.

The spinal implant system can include one or more of an adjustable end cap 10 as depicted in FIGS. 1-6, and possibly, a spinal implant or spinal implants. The spinal implant, for example, can be a corpectomy device 12 depicted in FIGS. 7-11. The end cap 10 can be used with additional end caps 10 and/or a spinal implant or spinal implants such as the corpectomy device 12. For example, multiple end caps 10 can be stacked on top of one another, as depicted in FIG. 6. Furthermore, the componentry of the spinal implant system can be assembled outside of the body, in situ within the spine, or a combination of outside and in situ assembly.

To illustrate, for example, the end cap 10 can be attached to a first end of the corpectomy device 12, and a second end cap 10' (identical to the end cap 10) can be attached to a second end of the corpectomy device 12. Thus, one or more of the end caps 10 can be attached to either end of a spinal implant such as, for example, the corpectomy device 12. The spinal implant used with the end cap 10 can be unexpandable and expandable. Thus, while the corpectomy device 12 depicted in FIGS. 7-11 is expandable, corpectomy devices that are unexpandable can be used with one or more of the end caps 10. The dimensions and ultimate angularity of the spinal implant system implanted into a patient can vary at least depending on the size of the spinal implant, on whether the spinal implant is expandable or unexpandable, the number of the end caps utilized, and the angularity afforded by the spinal implant and the one or more end caps.

The end cap 10, as depicted in FIGS. 1-6, includes a base portion 14 and a body portion 16. As discussed below, the base portion 14 can be attached to the corpectomy device 12, and the body portion 16 can be positioned and repositioned with respect to the base portion 14 to afford adjustable angularity. That is, the body portion 16 is adjustable between different angled orientations with respect to the base portion 14.

Figure 1:
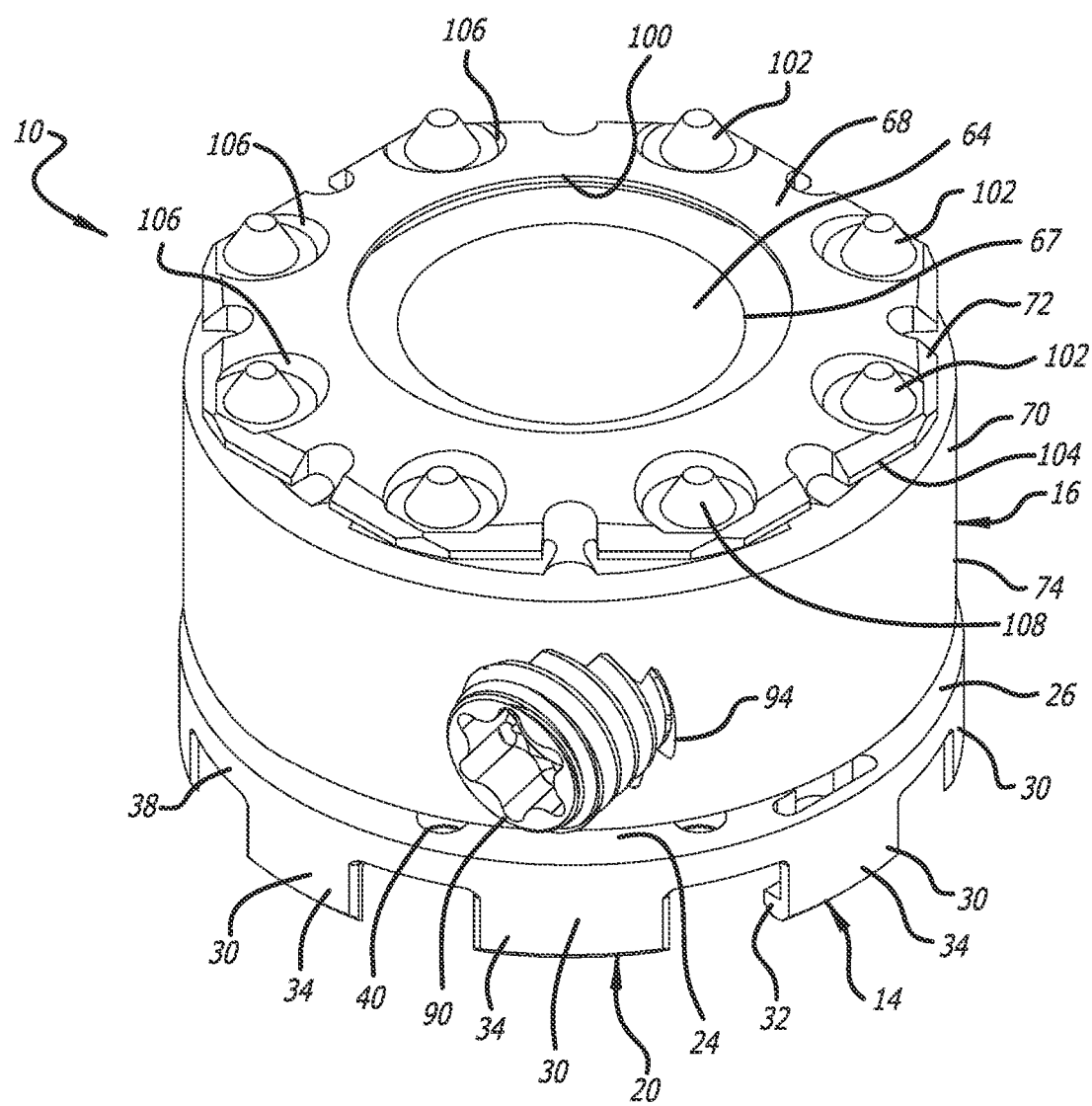
FIG. 1 is a top front perspective view of an end cap according to an embodiment of the present invention, the end cap including a base portion and a body portion that are adjustable with respect to one another.
Figure 1A:
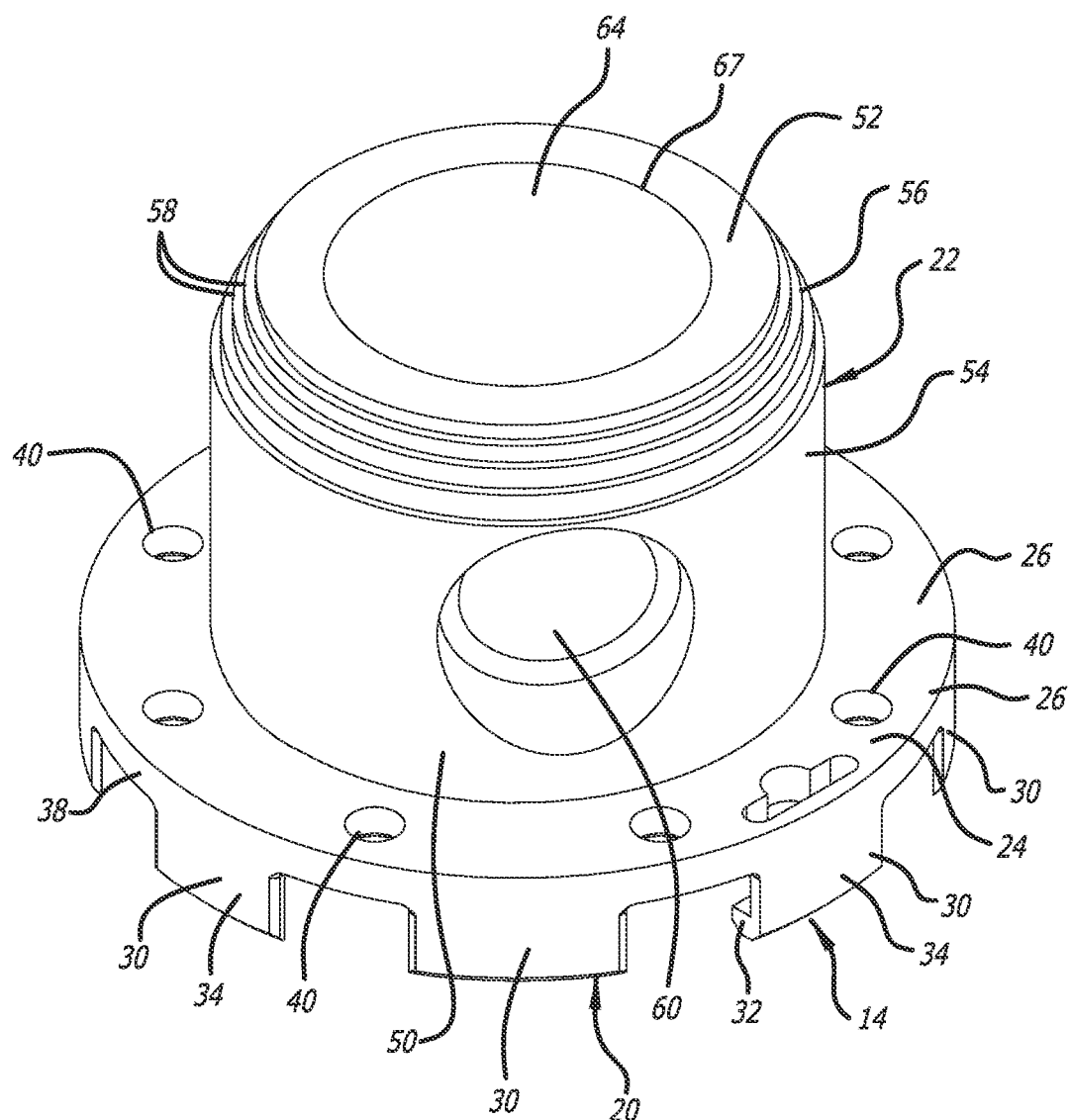
FIG. 1A is a top front perspective view of the base portion of the end cap of FIG. 1.
Figure 2:
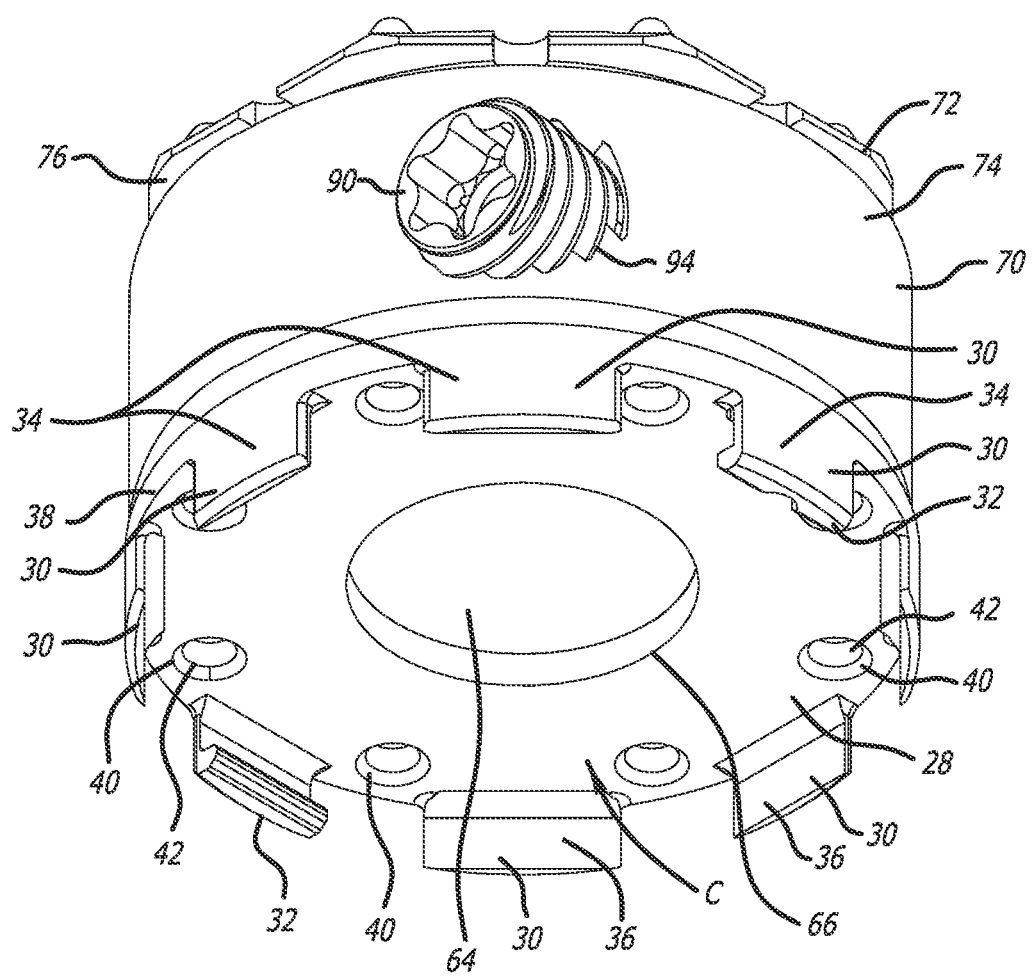
FIG. 2 is a bottom front perspective view of the end cap of FIG. 1.
Figure 3:
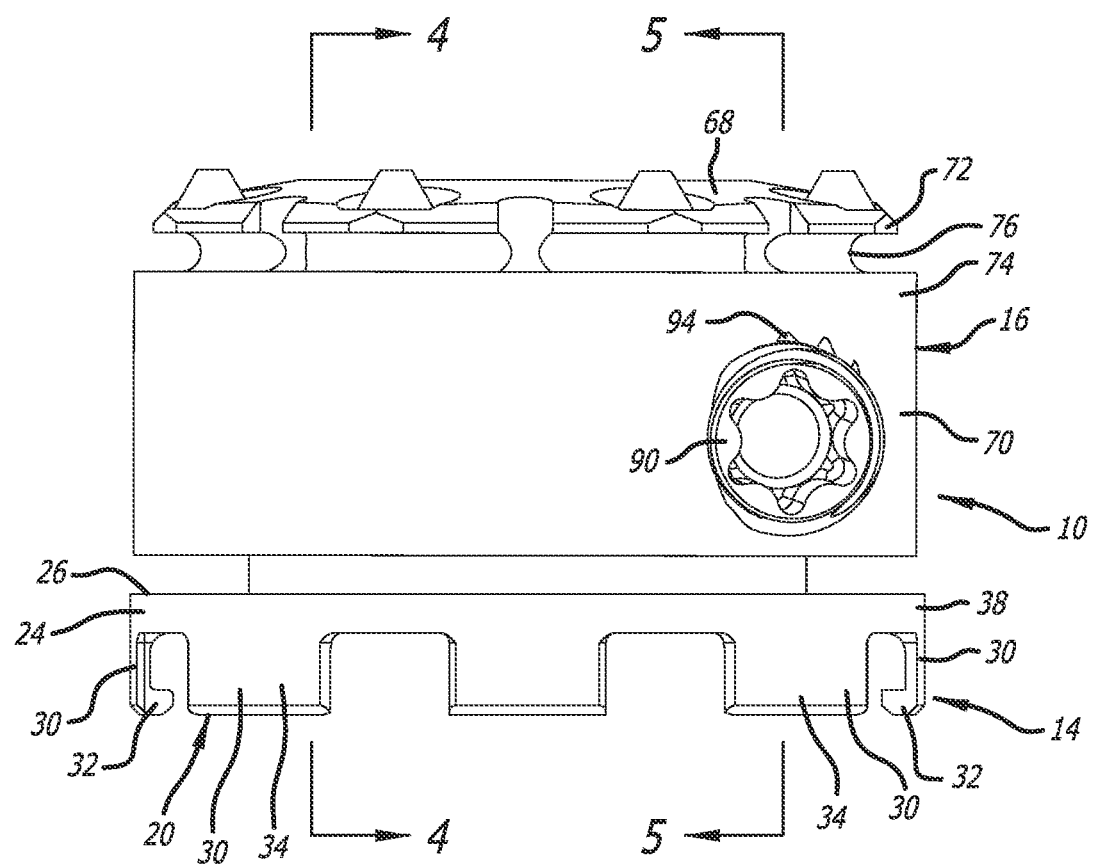
FIG. 3 is a front elevational view of the end cap of FIG. 1.

As depicted in FIGS. 1A and 4-5, the base portion 14 includes a lower portion 20 and an upper portion 22. As discussed below, the lower portion 20 is attachable and detachable to the corpectomy device 12. Furthermore, the upper portion 22 is attached to and extends upwardly from the lower portion 20, and the upper portion 22 serves as a pedestal for supporting the body portion 16 on the base portion 14.

The lower portion 20 includes a plate (or disc) portion 24, and the plate portion 24 includes an upper surface 26 and a lower surface 28. Various sidewall portions 30 extend downwardly from the lower surface 28, and at least two of the sidewall portions 30 include tabs 32 formed thereon facilitating the attachment and detachment of the end cap 10 to the second end cap 10' or the corpectomy device 12. The sidewall portions 30 are spaced apart from one another and include exterior surfaces 34 and interior surfaces 36. The exterior surfaces 34 and an exterior surface 38 of the plate portion 24 can be arcuate.

The lower surface 28 of plate portion 24 and the interior surfaces 36 of the sidewall portions 30 define a cavity C for receiving a portion of the second end cap 10' or a portion of the corpectomy device 12 therein. As discussed below, the tabs 32 facilitate attachment and detachment of the end cap 10 to the portions of the second end cap 10' or the corpectomy device 12 after these portions are received in the cavity C. Furthermore, the lower surface 28 of the plate portion 24 and interior surfaces 36 of the sidewall portions 30 are used to contact the portions of the second end cap 10' or the corpectomy device 12 received in the cavity C to resist movement of the end cap 10 with respect thereto. The sidewall portions 30 including the tabs 32 can have a degree of resiliency (or springiness) allowing passage of portions of the second end cap 10' or the corpectomy device 12 thereby. As such, the sidewall portions including the tabs 32 serve in attaching and detaching the end cap 10 to the second end cap 10' or the corpectomy device 12, and the sidewall portions 30 serve in stabilizing the position of the end cap 10 thereon.

The plate portion 24 includes various apertures 40 extending between the upper surface 26 and the lower surface 28 that can receive portions of the second end cap 10' or the corpectomy device 12. The apertures 40 are spaced apart from one another around the plate portion 24, and the apertures 40 can include engagement surfaces 42 adjacent the lower surface 28 for contacting complementary engagement surfaces on the second end cap 10' or the corpectomy device 12. The engagement surfaces 42 can have frusto-conical shapes. Rather than the various apertures 40, various depressions that incorporate the engagement surfaces 42 can be formed in the lower surface 28.

As discussed below, the upper portion 22 serves as a pedestal for supporting the body portion 16 on the base portion 14. The upper portion 22 includes a first end 50, an opposite second end 52, and an axis $A_1$ extending through the first end 50 and the second end 52. The first end 50 is attached to the plate portion 24, and the upper portion 22 extends from the plate portion 24 to the second end 52. As depicted in FIGS. 1A and 4-5, the upper portion 22 from the first end to adjacent the second end 52 includes an exterior surface portion 54, and at and adjacent the second end 52 includes an exterior surface portion 56. The exterior surface portion 54 can be substantially cylindrical, and the exterior surface portion 56 can have a decreasing taper. The decreasing taper, for example, can be formed by a plurality of steps 58 similar to those disclosed in U.S. Publication No. 2016/0100955, which is hereby incorporated by reference herein in its entirety.

The base portion 14 includes a passage 64 extending therethrough. The passage 64 extends through the lower portion 20 and the upper portion 22. The passage 64 includes a first opening 66 formed in the lower surface 28 of the plate portion 24 of the lower portion 20, and includes a second opening 67 formed in the exterior surface portion 56 of the second end 52 of the upper portion 22. The passage 64 can be filled with bone growth promoting materials. Thus, after implantation of the spinal implant system, the bone growth promoting materials can stimulate bone growth through the spinal implant system.

Figure 4A:
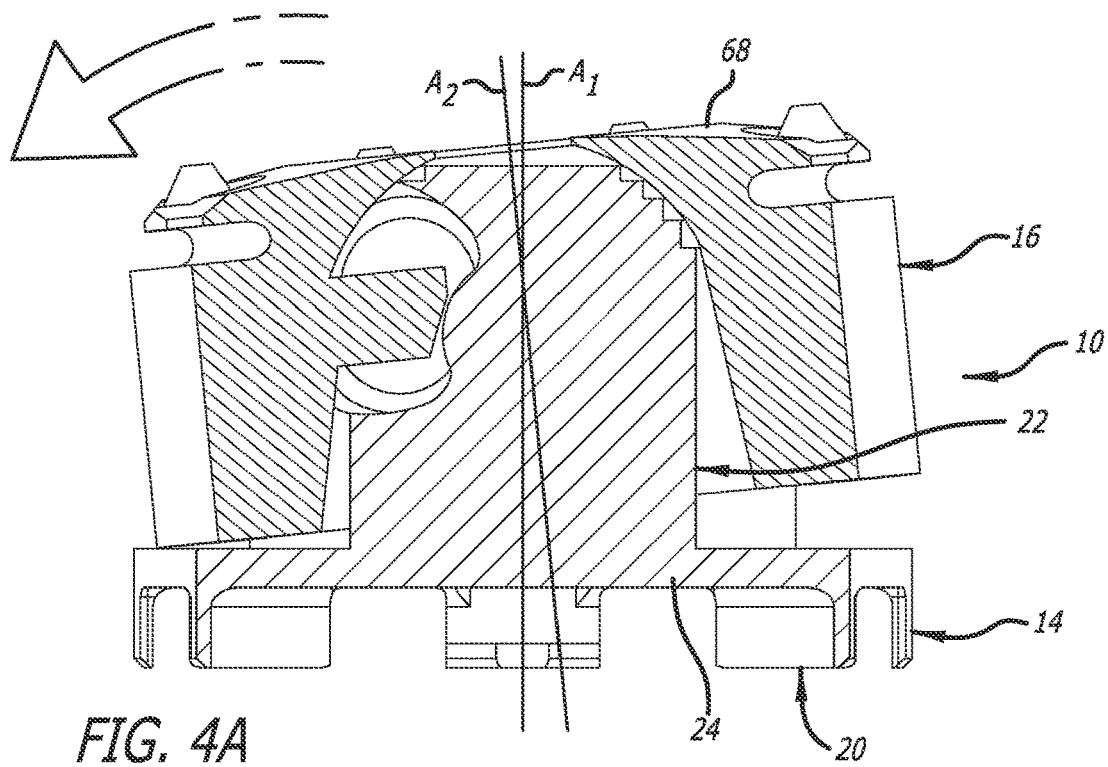
FIG. 4A is a cross-sectional view similar to that of FIG. 4 showing the body portion in a first orientation with respect to the base portion.
Figure 4B:
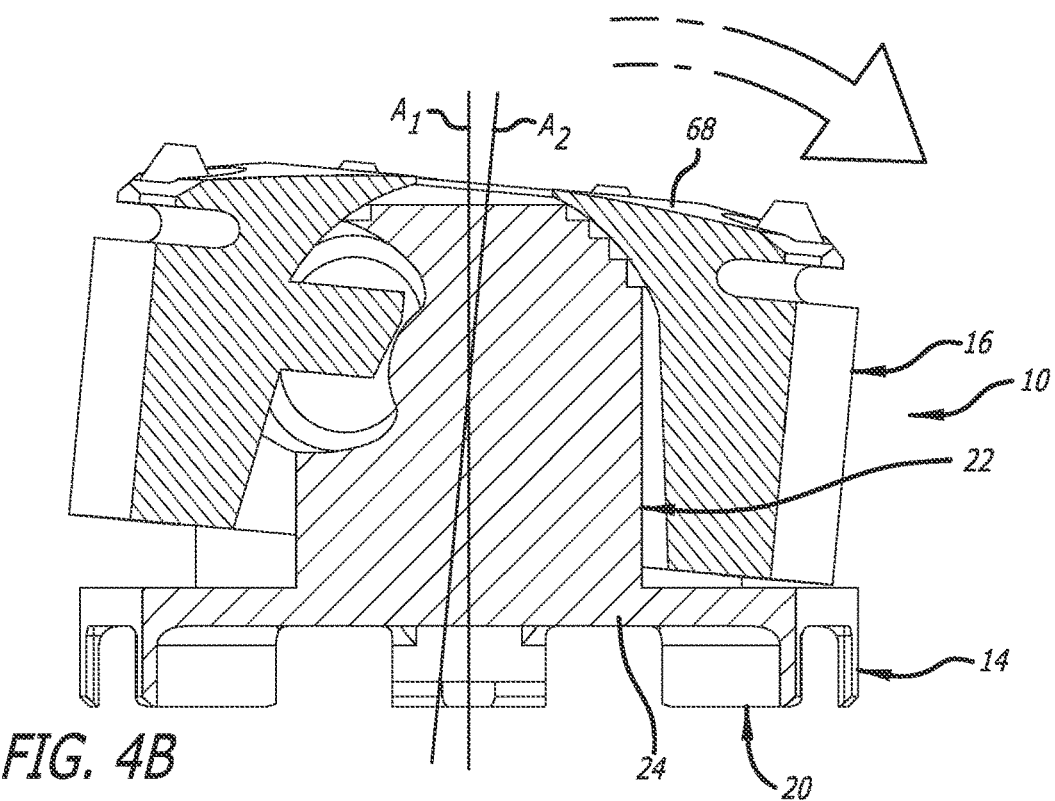
FIG. 4B is a cross-sectional view similar to that of FIG. 4 showing the body portion in a second orientation with respect to the base portion.

The plurality of steps 58 and the interior of the body portion 16 allow for selective positioning of the body portion 16 relative to the base portion 14. As depicted in FIGS. 4A and 4B, such selective positioning affords rotation of the body portion 16 relative to the axis $A_1$, and affords different angled orientations of the body portion 16 relative to the base portion 14. A top surface 68 of the body portion 16 can be angled at least in the range of ±10 degrees, if not more, relative to the axis $A_1$. Alternatively, an axis $A_2$ of the body portion 16 can be angled at least in the range of ±10 degrees, if not more, relative to the axis $A_1$. Furthermore, as discussed below, the body portion 16 can be fixed in position relative to the base portion 14 using a locking element 90 and a protrusion or nub 92 that impinge on a first engagement surface 60 and a second engagement surface 62, respectively, formed on the upper portion 22 similar to that disclosed in U.S. Publication No. 2016/0100955.

The body portion 16 includes a sidewall portion 70 and a flange portion 72. The sidewall portion 70 includes an exterior surface 74 that can be arcuate, and the radius of curvature of the exterior surface 74 can be similar to the radii of curvatures of the exterior surfaces 34 and the exterior surface 38. As depicted in FIGS. 1 and 2-4, the exterior surface 74 can be cylindrical. The sidewall portion 70 includes a recess 76 formed in the exterior surface 74 adjacent the flange portion 72. As depicted in FIGS. 1 and 2-4, the recess 76 can be annular.

The sidewall portion 70 also includes an interior surface 78 defining an interior cavity 80, and the interior cavity 80 is configured to receive a portion of the upper portion 22 of the base portion 14. The interior surface 78 includes a lower portion 82 that surrounds a portion the exterior surface portion 54, and the interior surface 78 includes an upper portion 84 for engaging the exterior surface portion 56. The lower portion 82 can have a frusto-conical shape, and the upper portion 84 can have a dome shape. The frusto-conical shape of the lower portion 82 and the dome shape of the upper portion 84 allow the body portion 16 to rotate on the upper portion 22 relative to the base portion 14 between the above-discussed angles.

The locking element 90 and the protrusion 92 can be used in fixing the body portion 16 in position relative to base portion 14. The locking element 90 can be a fastener such as a set screw received in an aperture 94 extending through the sidewall portion 70 of the body portion 16. The aperture 94 includes threads that complement the threads of the set screw 90, and the set screw 90 can be driven through the aperture 94 to impinge on the first engagement surface 60. Additionally, the protrusion 92 can be a nub that extends into the interior cavity 80 from the interior surface 78. The nub 92 can be engaged to the second engagement surface 62. The first engagement surface 60 and the second engagement surface 62 can be provided on opposite or approximately opposite sides of the upper portion 22, and the set screw 90 and the nub 92 can be provided on opposite or approximately sides of the body portion. Thus, impingement of the set screw 90 on the first engagement surface 60 causes impingement of the nub 92 on the second engagement surface 62. As such, the upper portion 22 can be clamped between the set screw 90 and the nub 92 by tightening of the set screw 90 to fix the body portion 16 in position relative to the base portion 14.

The flange portion 72 is configured to both engage bone of the patient and engage portions of the second end cap 10'. The flange portion 72 can engage an endplate of the vertebra of the patient, or the flange portion 72 can facilitate attachment of the end cap 10 to the second end cap 10' via receipt thereof in the cavity C of the second end cap 10'.

The flange portion 72 includes the top surface 68, an aperture 100 through the top surface 68, various protrusions 102 spaced apart from one another around the flange portion 72, and a perimeter surface 104 extending around the top surface 68. As depicted in FIG. 1, the aperture 100 ultimately affords access to the passage 64, and the various protrusions 102 extend upwardly from various recesses 106 formed in the top surface 68. The protrusions 102 include engagement surfaces 108 for either engaging the bone of the endplate of the patient, or engaging the complementary engagement surfaces 42 of the second end cap 10'. To illustrate, the engagement of the protrusions 102 (along with the recesses 106) to the bone of the endplate serves in resisting movement therebetween. Furthermore, the engagement of the engagement surfaces 108 of the end cap 10 with the engagement surfaces 42 of the second end cap 10' also serves in resisting movement therebetween.

To secure attachment therebetween, the flange portion 72 of the end cap 10 can be received in the cavity C of the second end cap 10'. In doing so, the engagement surfaces 108 of the end cap 10, as discussed above, are engaged to engagement surfaces 42 of the second end cap 10'. Furthermore, the top surface 68 of the end cap 10 is contacted with the lower surface 28 of the second end cap 10', portions of the perimeter surface 104 of the end cap 10 are contacted to the interior surfaces 36 of the sidewall portions 30 of the second end cap 10', and the recess 76 of the end cap 10 can receive the tabs 32 of the second end cap 10'.

As discussed above, the sidewall portions 30 including the tabs 32 have a degree of resiliency. Such resiliency allows the sidewall portions 30 including the tabs 32 to move between a first position and a second position, while being biased in the first position. As such, the sidewall portions 30 including the tabs 32 allow passage of the flange portion 72 thereby via movement thereof from the first position to the second position. Thereafter, the bias thereof moves the sidewall portions 30 including the tabs 32 back into the first position. The resiliency of the sidewall portions 30 including the tabs 32 allows the end cap 10 to be rocked (via the application of a rocking force) or snapped (via application of a linear force) into position on the second end cap 10'. When the sidewall portions 30 including the tabs 32 are in the first position, the tabs 32 can be received in the recess 76 to attach the end cap 10 to the second end cap 10'. Attachment can also be accomplished utilizing attachment mechanisms similar to those disclosed in U.S. Pat. No. 9,427,325, which is hereby incorporated by referenced herein in its entirety.

As depicted in FIG. 6, a third end cap 10" (identical to the end cap 10) can be attached to the second end cap 10', and a fourth end cap 10'" (identical to the end cap 10) to the third end cap 10" in a similar manner to the attachment of the second end cap 10' to the end cap 10. As such, various end caps 10 can be stacked on top of one another. The stacking of additional end caps 10 increases the height of the assembly and also increases the potential angularity of the assembly.

Additionally, the cavities C of the end cap 10 or the second end cap 10' can receive a first flange portion 110 or a second flange portion 112 of an expandable spinal implant such as, for example, the corpectomy device 12. The corpectomy device 12 is similar to that disclosed in U.S. Publication No. 2016/0100955. Like the device disclosed in U.S. Publication No. 2016/0100955, the overall height of the corpectomy device 12 is adjustable between an unexpanded configuration and an expanded configuration, and at least one end of the corpectomy device includes features affording adjustable angularity. However, an unexpandable spinal implant such a corpectomy device having a fixed height and a fixed angularity could also be used.

Figure 7:
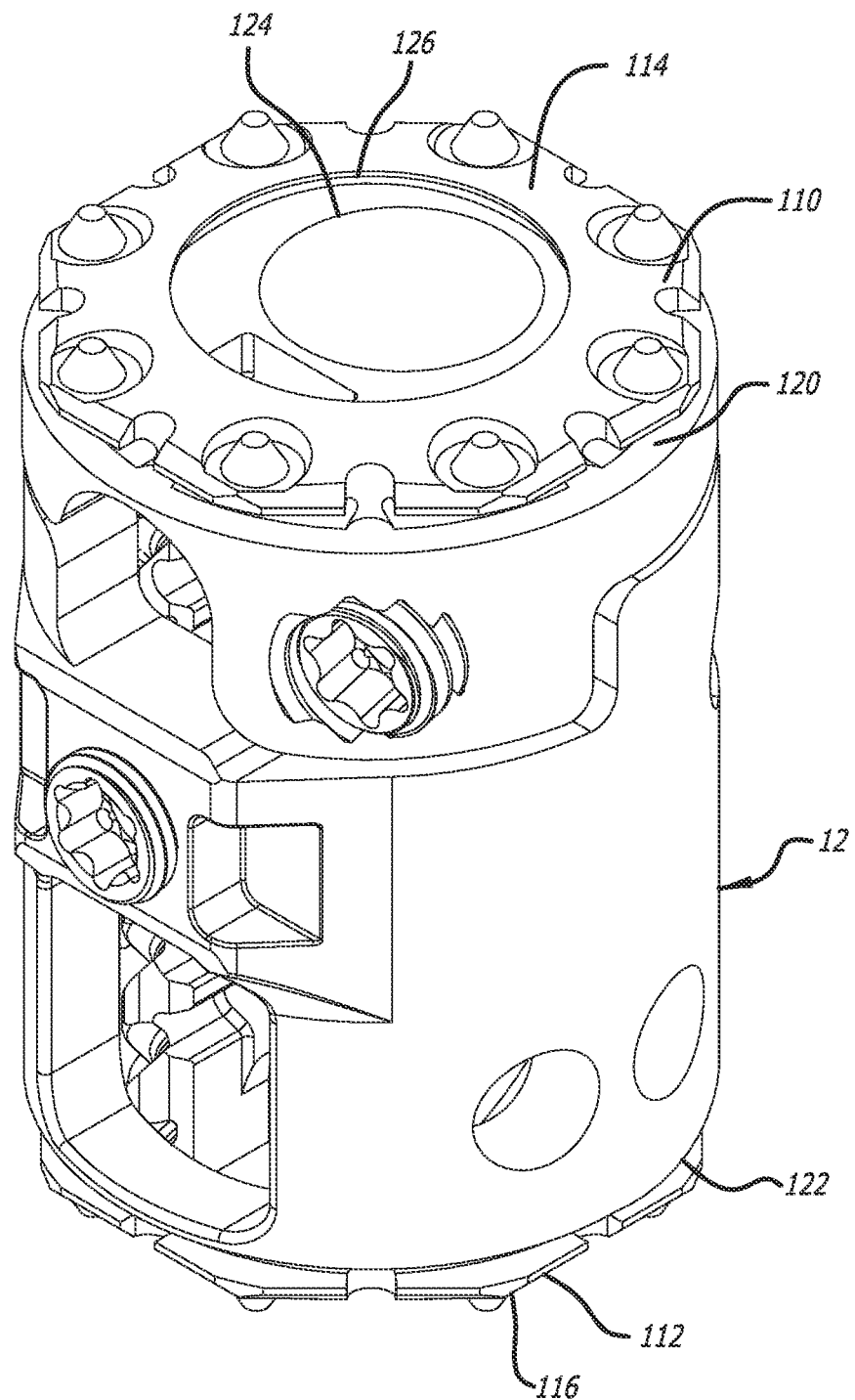
FIG. 7 is a top front perspective view of a corpectomy device usable together with the end cap of FIG. 1.
Figure 8:
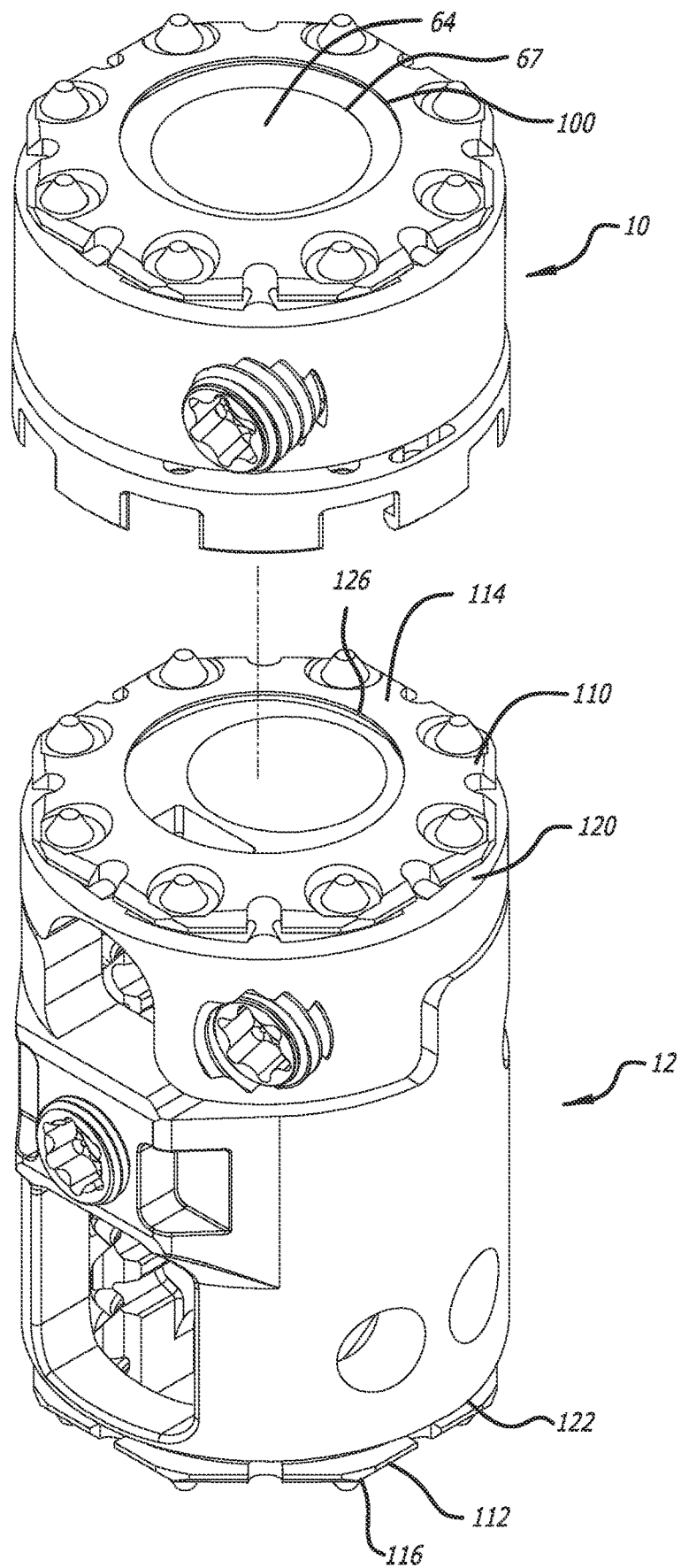
FIG. 8 is a top front exploded perspective view of the end cap of FIG. 1 positioned for attachment to the corpectomy device of FIG. 7.
Figure 9:
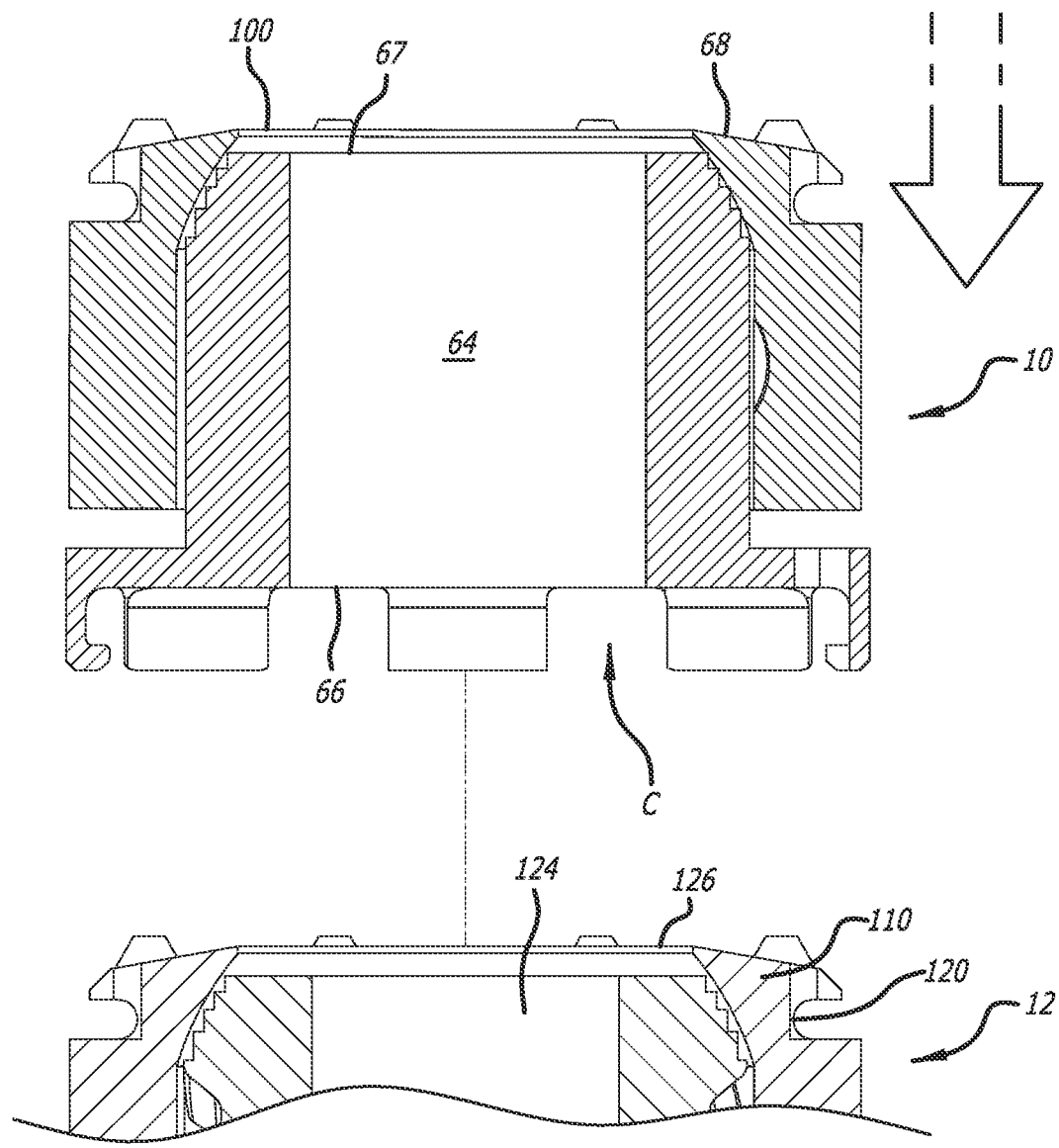
FIG. 9 is a cross-sectional view of the end cap of FIG. 1 and a portion of the corpectomy device of FIG. 7, where the end cap is positioned for attachment to the corpectomy device.
Figure 10:
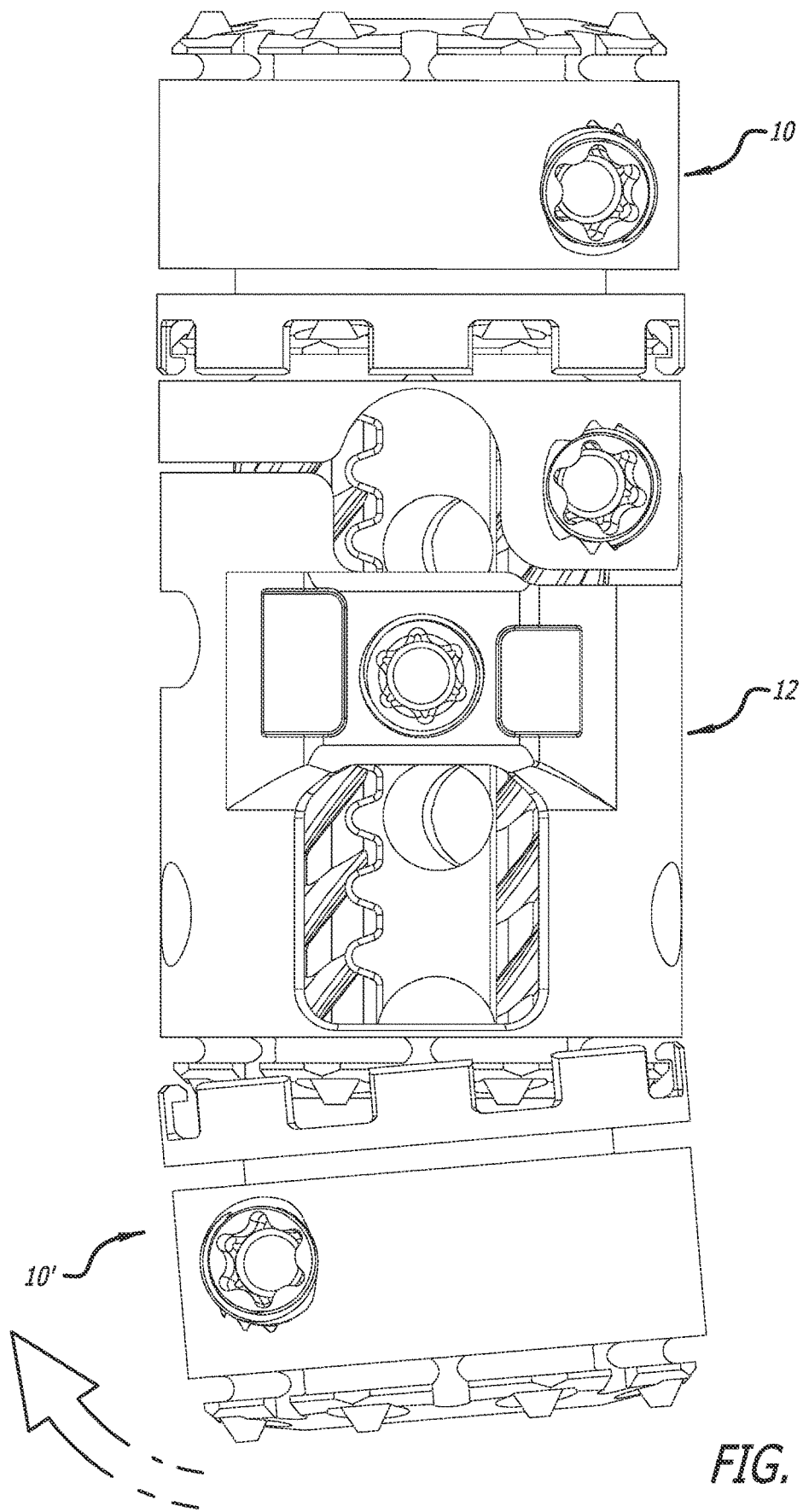
FIG. 10 is a front elevational view of another end cap of FIG. 1 being attached to the corpectomy device of FIG. 7.
Figure 11:
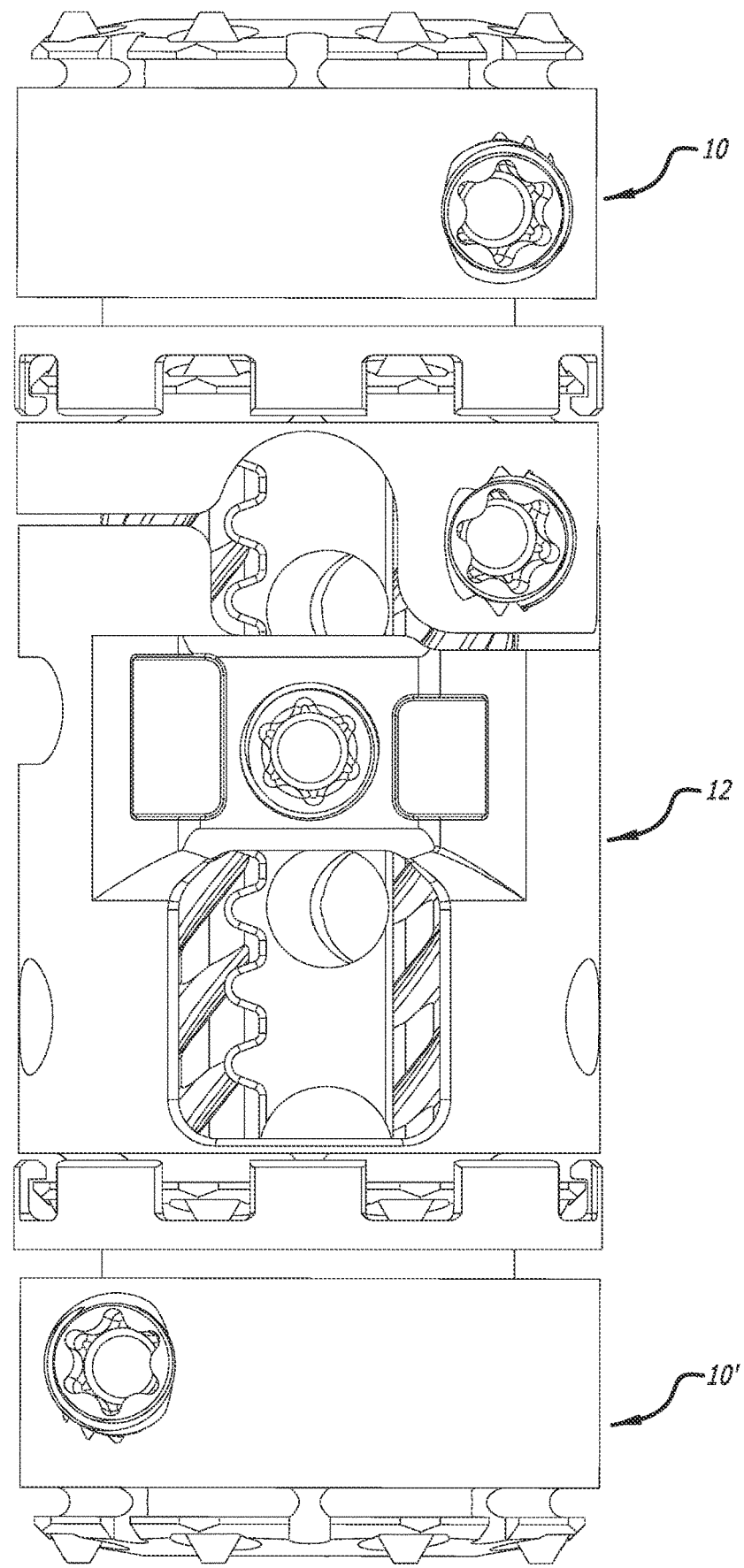
FIG. 11 is a front elevational view of the another end cap of FIG. 1 attached to the corpectomy device of FIG. 7.

As depicted in FIGS. 7 and 8, the corpectomy device 12 includes a first end 114 at which the first flange portion 110 is provided, and includes an opposite second end 116 at which the second flange portion 112 is provided. A first recess 120 is provided adjacent the first flange portion 110, and a second recess 122 is provided adjacent the second flange portion 112. The first flange portion 110, the second flange portion 112, the first recess 120, and the second recess 122 could also be included on a fixed height spinal implant (such as, for example, a corpectomy device) in similar fashion. The first flange portion 110 and the second flange portion 112 are similar (if not identical) to the flange portion 72 of the end cap 10. FIGS. 8 and 9 depict, for example, the end cap 10 being positioned for attachment to the first flange portion 110. Furthermore, the end cap 10 can be attached to one of the first flange portion 110 and the second flange portion 112, and the second end cap 10' can be attached to the other of the first flange portion 110 and the second flange portion 112. As depicted in FIGS. 10 and 11, the end cap 10 is attached to the first flange portion 110 and the second end cap 10' is attached to the second flange portion 112.

While FIG. 10 depicts the end cap 10' being rocked into position via rocking force applied thereto, the end caps 10 and 10' can be snapped onto the first flange portion 110 and the second portion 112 via the application of linear force thereto. The sidewall portions 30 including tabs 32 formed thereon, as discussed above, include a degree of resiliency to facilitate the attachment of the end cap 10 and the end cap 10' via rocking and/or snapping thereon. Furthermore, the third end cap 10" and/or the fourth end cap 10'" can stacked onto the end cap 10 or the second end cap 10' in similar fashion. Thus, the height and angularity of the spinal implant system implanted into a patient can vary at least depending on the size of the corpectomy device, on whether the corpectomy device is expandable or unexpandable, the number of the end caps utilized, and the angularity afforded by the one or more end caps and the corpectomy device.

The corpectomy device 12 includes a passage 124 extending between the first end 114 and the second end 116 thereof. The passage 124 includes a first opening 126 in the first flange portion 110 at the first end 114 and a second opening (not shown) in the second flange portion 112 at the second end 116. Furthermore, the passage 124, like the passage 64 of the end cap 10, can be filled with bone growth promoting materials. Thus, when one or more end caps 10 are attached to the corpectomy device 12, the passage(s) 64 and the passage 124 can communicate with one another. As such, after implantation of the spinal implant system, the bone growth promoting materials provided in the passage 64 and the passage 124 can be used to promote bone growth between the vertebral bodies bordering the intervertebral space. Thus, after implantation of the spinal implant system, the bone growth promoting materials can stimulate bone growth through the spinal implant system.

The spinal implant system can employ one or more of the end caps 10 and a spinal implant such as, for example, the corpectomy device 12 is for implantation into a section of the spine of the patient. The intervertebral space can be formed by removal of one or more vertebral bodies and one or more discs, and the spinal implant system is used to bridge the intervertebral space between the vertebral bodies bordering the intervertebral space. When using the spinal implant system of the present invention, the distance and the angularity between the vertebral bodies bordering the intervertebral space is determined. A corpectomy device 12 having an appropriate height, and one or more of the end caps 10 can be attached to either end of the corpectomy device 12 to provide a height of the spinal implant system sized in accordance with the distance between the vertebral bodies bordering the intervertebral space. Furthermore, angularity of the end caps 10 can be adjusted to accommodate the angularity between the vertebral bodies bordering the intervertebral space. The height of the spinal implant system also can be adjusted via use of an expandable, as opposed to an unexpandable, spinal implant, and the angularity of the spinal implant system also can be adjusted using a spinal implants including features affording adjustable angularity.

Furthermore, the spinal implant system can employ one or more of the end caps 10 and a plurality of spinal implants such as, for example, a plurality of the corpectomy devices. For example, at least one of the end caps 10 can be used with at least two corpectomy devices. To illustrate, the end cap 10 could be positioned between a first one and a second one of the corpectomy devices. The end cap 10 could be attached to a first corpectomy device such as, for example, the corpectomy device 12 via receipt of the first flange portion 110 of the corpectomy device 12 in the cavity C of the end cap 10. Furthermore, a second corpectomy device could be modified to have structure providing a cavity similar to the cavity C of the end cap 10, and the end cap 10 could be attached to the second corpectomy device via receipt of the flange portion 72 in the cavity of the second corpectomy device. Rather than modifying the second corpectomy to have structure providing a cavity similar to the cavity C of the end cap 10, the end cap 10 could be modified to include structure providing a second cavity similar to the cavity C instead of the flange 72, and the first flange 110 of the first corpectomy device could be received in the cavity C, and the second flange 112 of the second corpectomy device could be received in the second cavity similar to cavity C. Alternatively, the end cap 10 could be modified to include structure providing a second flange similar to flange 72 instead of the cavity C, the first corpectomy device and the second corpectomy device could be modified to have structure providing cavities similar to the cavity C, and the flange 72 could be received in the cavity of the first corpectomy device, and the second flange similar to flange 72 could received in the cavity of the second corpectomy devices. Other types of implants can be similarly modified. Additionally, additional end caps 10 and additional spinal implants could be modified and attached to one another in similar fashion.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An end cap comprising:
a first end, an opposite second end, a base portion, and a body portion,
the base portion including a lower portion and an upper portion, the lower portion being provided at the first end of the end cap, and the upper portion extending from the lower portion to adjacent the second end of the end cap,
the lower portion including a first end, an opposite second end, a perimeter, a mid-longitudinal axis extending through the first end and the second end, a lower surface, and a plurality of sidewall portions, the plurality of sidewall portions of the lower portion being spaced apart from one another adjacent the perimeter of the lower portion, the plurality of sidewall portions of the lower portion including inner surfaces, and at least two of the plurality of sidewall portions of the lower portion being spaced apart from one another across a portion of the lower surface, the lower surface and the inner surfaces of the plurality of sidewall portions of the lower portion defining a cavity, the inner surfaces of at least two of the plurality of sidewall portions of the lower portion each including a tab extending into the cavity, and the lower portion having a maximum dimension perpendicular to the mid-longitudinal axis of the lower portion in a first plane extending through the plurality of sidewall portions, and
the upper portion including a first end, an opposite second end, a mid-longitudinal axis extending through the first end and the second end of the upper portion, and an exterior surface extending between the first end and the second end, the first end of the upper portion being attached to the lower portion, the upper portion having a maximum dimension perpendicular to the mid-longitudinal axis of the upper portion in a second plane extending through the exterior surface that is less than the maximum dimension of the lower portion, the exterior surface including a tapered portion adjacent the second end of the upper portion having a first step portion and a second step portion, and the tapered portion residing in a third plane and a fourth plane that are perpendicular to the mid-longitudinal axis of the upper portion, the tapered portion having a maximum dimension in the third plane extending through the first step portion, and a maximum dimension in the fourth plane extending through the second step portion, the maximum dimension in the fourth plane being less than the maximum dimension in the first plane, and the second step portion being closer to the second end than the first step portion, and
the body portion including a sidewall portion, a flange portion, and a recess, the sidewall portion extending from adjacent the first end of the end cap to adjacent the second end of the end cap, the flange portion being provided at the second end of the end cap, and the recess provided in the sidewall portion adjacent the flange portion, the sidewall portion having a mid-longitudinal axis and defining an interior cavity for receiving a portion of the upper portion of the base portion, the interior cavity having an engagement surface therein for contacting at least a portion of the tapered portion of the upper portion of the base portion;
wherein the body portion is positionable with respect to the base portion by adjusting the position of the engagement surface of the interior cavity of the body portion on the tapered portion of the upper portion of the base portion; and
wherein the cavity of the end cap is configured to receive one of a second flange portion of a spinal implant and a third flange of a second end cap similar to the end cap, the tabs of the end cap are configured to be received in a corresponding one of a second recess of the spinal implant and a third recess of the second end cap similar to the end cap to facilitate attachment of the end cap to a corresponding one of the spinal implant and the second end cap similar to the end cap.

2. The end cap of claim 1, wherein each of the at least two of the plurality of sidewall portions of the lower portion including the tabs are moveable between a first position where the tabs are received in the one of the second recess of the spinal implant and the third recess of the second end cap similar to the end cap, and a second position that allows the one of the second flange portion of the spinal implant and the third flange portion of the second end cap similar to the end cap to pass thereby, the at least two of the plurality of sidewall portions of the lower portion each being resiliently biased to the first position.

3. The end cap of claim 1, wherein the sidewall portion of the body portion includes an exterior surface and an aperture extending from the exterior surface to the interior cavity, and the end cap further comprises a fastener received in the aperture for impinging on the upper portion of the base portion, impingement of the fastener on the exterior surface of the upper portion of the base portion serving to fix the position of the body portion with respect to the base portion.

4. The end cap of claim 1, wherein the flange portion includes an upper surface, and the upper surface of flange portion moves relative to the mid-longitudinal axis of the upper portion at least ±10 degrees via positioning of the body portion relative to the base portion.

5. The end cap of claim 1, wherein the mid-longitudinal axis of the sidewall portion is moveable relative to the mid-longitudinal axis of the upper portion at least ±10 degrees via positioning of the body portion relative to the base portion.

6. The end cap of claim 1, wherein portions of the engagement surface are arcuate in a fourth plane and a fifth plane extending through the mid-longitudinal axis of the sidewall portion.

7. The end cap of claim 1 in combination with the second end cap, the second end cap comprising:
 a first end, an opposite second end, a base portion, and a body portion,
 wherein the body portion of the second end cap includes a sidewall portion, the third flange portion, and the third recess, the sidewall portion of the second end cap extending from adjacent the first end of the second end cap to adjacent the second end of the second end cap, the third flange portion being provided at the second end of the second end cap, and the third recess provided in the sidewall portion adjacent the third flange portion; and
 wherein the third flange of the second end cap is received in the cavity of the end cap, and the tabs of the end cap are received in the third recess of the second end cap.

8. The combination of end cap and the second end cap of claim 7,
 wherein the base portion of the second end cap includes a lower portion and an upper portion, the lower portion of the second end cap being provided at the first end of the second end cap, and the upper portion of the second end cap extending from the lower portion of the second end cap to adjacent the second end of the second end cap,
  the lower portion of the second end cap including a first end, an opposite second end, a perimeter, a mid-longitudinal axis extending through the first end and the second end of the second end cap, a lower surface, and a plurality of sidewall portions, the plurality of sidewall portions of the lower portion of the second end cap being spaced apart from one another adjacent the perimeter of the lower portion of the second end cap, the plurality of sidewall portions of the lower portion of the second end cap including inner surfaces, and at least two of the plurality of sidewall portions of the lower portion of the second end cap being spaced apart from one another across a portion of the lower surface of the second end cap, the lower surface and the inner surfaces of the plurality of sidewall portions of the lower portion of the second end cap defining a cavity, the inner surfaces of at least two of the plurality of sidewall portions of the lower portion of the second end cap each including a tab extending into the cavity of the second end cap, and the lower portion of the second end cap having a maximum dimension perpendicular to the mid-longitudinal axis of the lower portion of the second end cap in a fifth plane extending through the plurality of sidewall portions, and
  the upper portion of the second end cap including a first end, an opposite second end, a mid-longitudinal axis extending through the first end and the second end of the upper portion of the second end cap, and an exterior surface extending between the first end and the second end of the second end cap, the first end of the upper portion of the second end cap being attached to the lower portion of the second end cap, the upper portion of the second end cap having a maximum dimension perpendicular to the mid-longitudinal axis of the upper portion of the second end cap in a sixth plane extending through the exterior surface of the second end cap that is less than the maximum dimension of the lower portion of the second end cap, the exterior surface of the second end cap including a tapered portion adjacent the second end of the upper portion of the second end cap having a first step portion and a second step portion, and the tapered portion of the second end cap residing in a seventh plane and an eighth plane that are perpendicular to the mid-longitudinal axis of the upper portion of the second end cap, the tapered portion of the second end cap having a maximum dimension in the seventh plane extending through the first step portion of the second end cap, and a maximum dimension in the eighth plane extending through the second step portion of the second end cap, the maximum dimension in the eighth plane being less than the maximum dimension in the fifth plane, and the second step portion of the second end cap being closer to the second end of the second end cap than the first step portion of the second end cap;
 wherein the sidewall portion of the second end cap has a mid-longitudinal axis and defines an interior cavity for receiving a portion of the upper portion of the base portion of the second end cap, the interior cavity of the second end cap having an engagement surface therein for contacting at least a portion of the tapered portion of the upper portion of the base portion of the second end cap.

9. The combination of the end cap and the second end cap of claim 8, wherein the end cap is rotatably attached to the second end cap and capable of rotation by rotating the cavity with respect to the third flange.

10. The combination of the end cap and the second end cap of claim 8, wherein the sidewall portion of the body portion of the second end cap includes an exterior surface and an aperture extending from the exterior surface of the second end cap to the interior cavity of the second end cap, and the second end cap further comprises a fastener received in the aperture of the second end cap for impinging on the upper portion of the base portion of the second end cap, impingement of the fastener of the second end cap on the exterior surface of the upper portion of the base portion of the second end cap serving to fix the position of the body portion of the second end cap with respect to the base portion of the second end cap.

11. An end cap comprising:
a first end, an opposite second end, a base portion, and a body portion,
the base portion including a lower portion and an upper portion, the lower portion being provided at the first end of the end cap, and the upper portion extending from the lower portion to adjacent the second end of the end cap,
the lower portion including a first end, an opposite second end, a perimeter, a mid-longitudinal axis extending through the first end and the second end, a lower surface, and a plurality of sidewall portions, the plurality of sidewall portions of the lower portion being spaced apart from one another adjacent the perimeter of the lower portion, the plurality of sidewall portions of the lower portion including inner surfaces, and at least two of the plurality of sidewall portions of the lower portion being spaced apart from one another across a portion of the lower surface, the lower surface and the inner surfaces of the plurality of sidewall portions of the lower portion defining a cavity, the inner surfaces of at least two of the plurality of sidewall portions of the lower portion each including a tab extending into the cavity, and the lower portion having a maximum dimension perpendicular to the mid-longitudinal axis of the lower portion in a first plane extending through the plurality of sidewall portions, and
the upper portion including a first end, an opposite second end, a mid-longitudinal axis extending through the first end and the second end of the upper portion, and an exterior surface extending between the first end and the second end, the first end of the upper portion being attached to the lower portion, the upper portion having a maximum dimension perpendicular to the mid-longitudinal axis of the upper portion in a second plane extending through the exterior surface that is less than the maximum dimension of the lower portion, the exterior surface including a tapered portion adjacent the second end of the upper portion having a first step portion and a second step portion, and the tapered portion residing in a third plane and a fourth plane that are perpendicular to the mid-longitudinal axis of the upper portion, the tapered portion having a maximum dimension in the third plane extending through the first step portion, and a maximum dimension in the fourth plane extending through the second step portion, the maximum dimension in the fourth plane being less than the maximum dimension in the first plane, and the second step portion being closer to the second end than the first step portion, and
the body portion including a sidewall portion, a flange portion, and a recess, the sidewall portion extending from adjacent the first end of the end cap to adjacent the second end of the end cap, the flange portion being provided at the second end of the end cap, and the recess provided in the sidewall portion adjacent the flange portion, the sidewall portion having a mid-longitudinal axis and defining an interior cavity for receiving a portion of the upper portion of the base portion, the interior cavity having an engagement surface therein for contacting at least a portion of the tapered portion of the upper portion of the base portion;
wherein the body portion is positionable with respect to the base portion by adjusting the position of the engagement surface of the interior cavity of the body portion on the tapered portion of the upper portion of the base portion.

12. The end cap of claim 11, wherein each of the at least two of the plurality of sidewall portions of the lower portion including the tabs are moveable between a first position where the tabs are received in one of a second recess of a spinal implant and a third recess of a second end cap similar to the end cap, and a second position that allows one of a second flange portion of the spinal implant and a third flange portion of the second end cap similar to the end cap to pass thereby, the at least two of the plurality of sidewall portions of the lower portion each being resiliently biased to the first position.

13. The end cap of claim 11, wherein the sidewall portion of the body portion includes an exterior surface and an aperture extending from the exterior surface to the interior cavity, and the end cap further comprises a fastener received in the aperture for impinging on the upper portion of the base portion, impingement of the fastener on the exterior surface of the upper portion of the base portion serving to fix the position of the body portion with respect to the base portion.

14. The end cap of claim 11, wherein the flange portion includes an upper surface, and the upper surface of third flange portion moves relative to the mid-longitudinal axis of the upper portion at least ±10 degrees via positioning of the body portion relative to the base portion.

15. The end cap of claim 11, wherein the mid-longitudinal axis of the sidewall portion is moveable relative to the mid-longitudinal axis of the upper portion at least ±10 degrees via positioning of the body portion relative to the base portion.

16. An end cap comprising:
a first end, an opposite second end, a base portion, and a body portion,
the base portion including a lower portion and an upper portion, the lower portion being provided at the first end of the end cap, and the upper portion extending from the lower portion to adjacent the second end of the end cap,
the lower portion including a first end, an opposite second end, a perimeter, a mid-longitudinal axis extending through the first end and the second end, a lower surface, and a plurality of sidewall portions having inner surfaces, the plurality of sidewall portions of the lower portion being spaced apart from one another adjacent the perimeter of the lower portion, the lower surface and the inner surfaces of the plurality of sidewall portions of the lower portion defining a cavity, the inner surfaces of at least two of the plurality of sidewall portions of the lower portion each including a tab extending into the cavity, and the lower portion having a maximum dimension perpendicular to the mid-longitudinal axis of the lower portion in a first plane extending through the plurality of sidewall portions, and
the upper portion including a first end, an opposite second end, a mid-longitudinal axis extending through the first end and the second end of the upper portion, and an exterior surface extending between the first end and the second end, the first end of the upper portion being attached to the lower portion, the exterior surface including a tapered portion adjacent the second end of the upper portion having a first step portion and a second step portion, a third plane perpendicular to the mid-longitudinal axis of the upper portion extending through the first step portion, and a fourth plane perpendicular to the mid-longitudinal axis of the upper portion extending through the second step portion, a maximum dimension in the third plane extending through the first step portion being greater than a maximum dimension in the fourth plane extending through the second step portion, and the body portion including a sidewall portion, a flange portion, and a recess, the sidewall portion extending from adjacent the first end of the end cap to adjacent the second end of the end cap, the flange portion being provided at the second end of the end cap, and the recess provided in the sidewall portion adjacent the flange portion, the sidewall portion having a mid-longitudinal axis and defining an interior cavity for receiving a portion of the upper portion of the base portion, the interior cavity having an engagement surface therein for contacting at least a portion of the tapered portion of the upper portion of the base portion;

wherein the body portion is positionable with respect to the base portion by adjusting the position of the engagement surface of the interior cavity of the body portion on the tapered portion of the upper portion of the base portion.

17. The end cap of 16, wherein each of the at least two of the plurality of sidewall portions of the lower portion including the tabs are moveable between a first position where the tabs are received in one of a second recess of a spinal implant and a third recess of a second end cap similar to the end cap, and a second position that allows the one of the second flange portion of the spinal implant and the third flange portion of the second end cap similar to the end cap to pass thereby, the at least two of the plurality of sidewall portions of the lower portion each being resiliently biased to the first position.

18. The end cap of claim 16, wherein the sidewall portion of the body portion includes an exterior surface and an aperture extending from the exterior surface to the interior cavity, and the end cap further comprises a fastener received in the aperture for impinging on the upper portion of the base portion, impingement of the fastener on the exterior surface of the upper portion of the base portion serving to fix the position of the body portion with respect to the base portion.

19. The end cap of claim 16, wherein the flange portion includes an upper surface, and the upper surface of third flange portion moves relative to the mid-longitudinal axis of the upper portion at least ±10 degrees via positioning of the body portion relative to the base portion.

20. The end cap of claim 16, wherein the mid-longitudinal axis of the sidewall portion is moveable relative to the mid-longitudinal axis of the upper portion at least ±10 degrees via positioning of the body portion relative to the base portion.

* * * * *